(12) United States Patent
Warren, Jr.

(10) Patent No.: US 8,343,048 B2
(45) Date of Patent: Jan. 1, 2013

(54) RETRACTOR SYSTEM

(75) Inventor: W. Lee Warren, Jr., Auburn, AL (US)

(73) Assignee: Lanx, Inc., Broomfield, CO (US)

( * ) Notice: Subject to any disclaimer, the term of this patent is extended or adjusted under 35 U.S.C. 154(b) by 1321 days.

(21) Appl. No.: 11/931,476

(22) Filed: Oct. 31, 2007

(65) Prior Publication Data

US 2008/0214898 A1 Sep. 4, 2008

Related U.S. Application Data

(60) Provisional application No. 60/855,645, filed on Oct. 31, 2006.

(51) Int. Cl.
*A61B 1/32* (2006.01)
(52) U.S. Cl. ....................................................... 600/233
(58) Field of Classification Search .................. 600/201, 600/210, 215, 216, 218–219, 222, 224, 235
See application file for complete search history.

(56) References Cited

U.S. PATENT DOCUMENTS

| | | | | |
|---|---|---|---|---|
| 5,944,658 | A * | 8/1999 | Koros et al. | 600/232 |
| 6,951,538 | B2 * | 10/2005 | Ritland | 600/210 |
| 2005/0159651 | A1 * | 7/2005 | Raymond et al. | 600/213 |
| 2006/0106416 | A1 * | 5/2006 | Raymond et al. | 606/198 |

* cited by examiner

*Primary Examiner* — Sameh Boles
(74) *Attorney, Agent, or Firm* — David G. Oberdick; Peter J. Borghetti

(57) ABSTRACT

The present invention provides a surgical retractor system in which first and second retractor blades are maintained in spaced relationship by a third retractor blade engaged with the first and second retractor blades. The first and second retractor blades are moveable between a first position in which they are nearer one another and a second position in which they are further from one another. The third retractor blade is engageable with the first and second retractor blades in the second position to maintain the first and second retractor blades in the second position. The first, second, and third retractor blades define an open space between them in which a minimally invasive surgical procedure may be carried out.

15 Claims, 10 Drawing Sheets

RETRACTOR SYSTEM

CROSS-REFERENCE TO RELATED APPLICATIONS

This application claims the benefit of U.S. Provisional Application No. 60/855,645, filed Oct. 31, 2006.

FIELD OF THE INVENTION

The invention relates to retractors for holding open an incision at a surgical site. In particular, the invention relates to retractors useful in minimally invasive surgery.

BACKGROUND

Surgical procedures often involve accessing surgical sites within the patient's body. The deeper the surgical site within the body, the more difficult it is to access and visualize the surgical site. In an open surgical procedure, a large incision is made and the tissues surrounding the site are pressed or pulled out of the way with one or more retractors to facilitate access. However, open procedures are very disruptive of the tissues surrounding the site and require extended recovery periods. It is increasingly common to perform surgery through minimally invasive approaches utilizing small incisions. What is needed is a retractor that can be deployed in a small incision to create and maintain a path to the surgical site with minimal disruption of surrounding tissues.

SUMMARY

The present invention provides a surgical retractor system in which first and second retractor blades are maintained in spaced relationship by a third retractor blade engaged with the first and second retractor blades. The retractor system is useful in minimally invasive surgery.

In one aspect of the invention, a retractor system for holding open an incision at a surgical site includes first and second retractor blades moveable between a first position in which they are nearer one another and a second position in which they are further from one another. A third retractor blade is engageable with the first and second retractor blades in the second position to maintain the first and second retractor blades in the second position. The first, second, and third retractor blades define an open space between them in which a surgical procedure may be carried out.

In another aspect of the invention, the distal end of the third retractor blade is engageable with the proximal end of the first and second retractor blades in distal sliding relationship.

In another aspect of the invention, the retractor system includes a guidance array trackable by a surgical navigation system to indicate the location of a retractor blade within the surgical environment.

In another aspect of the invention, a retractor system for defining a path to a surgical site on the anterior portion of the cervical spine includes separate first and second retractor blades moveable between a first position in which they are nearer one another and a second position in which they are further from one another. The first and second retractor blades each include a handle removably mounted to the blade. Third and fourth retractor blades are engageable with the first and second retractor blades in the second position to maintain the first and second retractor blades in the second position. The first, second, third, and fourth retractor blades define an open space between them in which a surgical procedure may be carried out. At least one of the first, second, third, and fourth retractor blades includes a fastener for engaging a cervical vertebra to secure the at least one blade to the vertebra.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Figure 1:
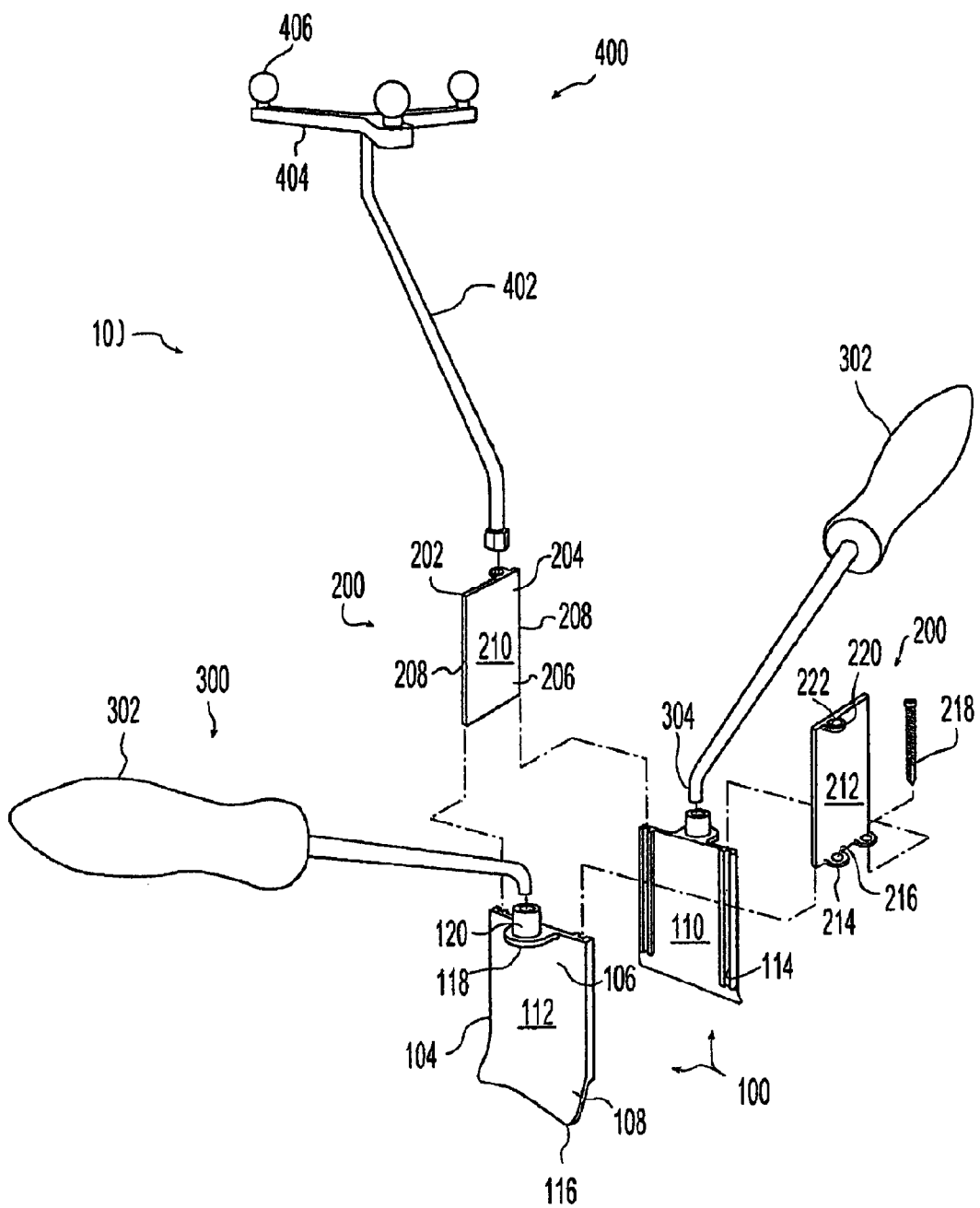
FIG. 1 is an exploded perspective view of an illustrative embodiment of a retractor system according to the present invention.

The retractor system and methods of the present invention may be utilized to gain access to a variety of surgical sites. Such sites may include the hip joint, knee joint, shoulder joint, elbow joint, ankle joint, digital joint of the hand or foot, fracture site, tumor site, vertebral body, disc space, pedicles, facet joints, spinal canal, spinal processes, abdominal cavity, and/or other surgical sites. The apparatus and methods may be utilized to approach the site from a variety of directions including anteriorly, posteriorly, laterally, obliquely, and/or other directions.

Embodiments of a retractor system according to the present invention include a plurality of retractor blades moveable between a first position in which they are nearer one another and a second position in which they are further from one another. The blades may be connected together by a mechanism that guides the motion of the blades relative to one another or the blades may be separate from one another and freely positionable relative to one another. The retractor system may further include one or more additional blades, or sidewalls, engageable with the first blades in the second position to maintain the first blades in the second position. The blades may have an insertion axis defined as an axis along which the blades are inserted into the surgical site. The blades may be flat, curved, arched, flared, cylindrical and/or any other suitable shape relative to the insertion axis. Likewise, the blades may be rectangular, triangular, round, random shaped, and/or any other suitable shape normal to the insertion axis. Preferably, the blades are shaped for ease of insertion along the insertion axis and for tissue retention when they are moved normal to the insertion axis. For example, in one embodiment, the blades are relatively flat along the insertion axis with outturned tips to grip tissue.

The blades may connect to form a friction fit, snap fit, dovetail fit, hinged connection, magnetic connection, pinned connection, hook and loop connection, and/or any other suitable connection. The blades may be assembled to form an open space in which a surgical procedure may be carried out. The open space may be defined by a continuous wall or an interrupted wall able to keep tissues from encroaching on the open space. For example the blades may be assembled to form a closed shape or an open shape. The assembled shape may be circular, oval, triangular, rectangular, trapezoidal, pentagonal, hexagonal, irregular, and/or any other suitable shape.

The blades may include tabs, spikes, screws, and/or other fastening aids to attach the blades to an underlying bone. For example, one or more blades may include one or more tabs able to receive a screw through the tab and into an underlying bone to attach the blade to the bone and support the blade in a stable position relative to the bone. The blades may include mounting fixtures for attaching accessories to the blades. Accessories may include handles, lights, guidance arrays, and/or other suitable accessories. For example, one or more blades may include a mount for a handle to facilitate manipulating the blades at the surgical site. Similarly, for example, one or more blades may include a mount for a guidance array trackable by a surgical navigation system to indicate within the navigation system the location of the blade and/or an underlying bone or other feature.

The blades may be made of any suitable material. For example, the blades may be made of polymers, metal, ceramic, and/or other suitable materials. Preferably the blades are radiolucent or radio transparent to allow unobstructed X-ray imaging during a surgical procedure. Also preferably, the blades are electrically non-conducting so as not to interfere with electrocautery, electrosurgery, and/or other electrical modalities. Likewise it is preferred that the blades are thermally non-conducting so as not to transmit heat, such as from a light source or electrocautery, to or from the surgical site. For example, plastic blades may be provided that are radiolucent and insulating. The blades may be disposable.

In the following detailed description of a preferred embodiment, the invention is illustrated in use in a particular form for accessing the anterior portion of the cervical spine of a human patient. However, the embodiments depicted are illustrative only and it is anticipated that the invention may be modified to access any surgical site in any patient.

FIG. 1 illustrates a retractor system 10 comprising a pair of opposing first and second blades 100, a pair of opposing third and fourth blades 200, a pair of handles 300, and a guidance array 400.

Each of the first and second blades 100 has a substantially flat rectangular body 104 extending along an insertion axis from a proximal end 106 to a distal end 108. Each blade has an inwardly directed face 110 and an outwardly directed face 112. The inwardly directed face 110 includes a longitudinal groove 114 extending parallel to the insertion axis adjacent each of the outer edges. The distal end 108 includes an outturned tip 116. The proximal end 106 includes a tab 118 defining a socket 120 for receiving an accessory.

Each of the third and fourth blades 200 has a substantially flat rectangular body 202 extending along an insertion axis from a proximal end 204 to a distal end 206 and extending normal to the insertion axis between lateral edges 208. Each blade 200 further includes an inwardly directed face 210 and an outwardly directed face 212. The distal end 206 includes a tab 214 defining a hole 216 for receiving a bone screw 218. The proximal end 204 includes a tab 220 defining a hole 222 for receiving an accessory. The lateral edges 208 of the third and fourth blades 200 engage the grooves 114 in the first and second blades so that the blades may be assembled into a tubular retractor body. The lateral edges may engage the grooves laterally and/or axially. Preferably, the lateral edges 208 are engaged with the grooves 114 by engaging the distal end of the lateral edges 208 with the proximal end of the grooves 114 and sliding the blades along the groove parallel to the insertion axis. In the illustrative embodiment of FIG. 1, the tabs 118, 214, 220 all project outwardly from the outwardly directed faces so that the inwardly directed faces are unobstructed. However, one or more of the tabs may project inwardly.

The handles 300 each include a grip 302 at one end and a plug 304 at an opposite end. The plug 304 engages the socket 120. The handles 300 may be permanently attached to the first and second blades 100. Preferably, the handles 300 removably engage the first and second blades 100 so that they may be used to position the blades and then be removed to provide unobstructed access to the surgical site. Preferably, the handles 300 engage the first and second blades 100 in axial and torque transmitting relationship. In one embodiment, the handles 300 and blades 100 define a detent engagement. Preferably, the grips 302 are offset proximally and laterally from the plugs 304 for easier manipulation.

The guidance array 400 adapts the retractor system 10 for use with a surgical navigation system. The guidance array 400 includes a support 402, a body 404, and one or more targets 406 attached to the body. The support 402 attaches to the blades such as by bolting to the tab 220 in one of the third and fourth blades 200. The targets are detectable by the surgical navigation system such that the three dimensional position of the targets can be related to a surgical navigation coordinate system. For example, the surgical navigation system may include multiple sensors at known locations that feed target position information to a computer. The computer may then use the position information from the multiple sensors to triangulate the position of each target within the surgical navigation coordinate system. The surgical navigation system can then determine the position and orientation of the blades 100, 200 by detecting the position and orientation of the guidance array and then resolving the position and orientation of the blades from the known relationship between the guidance array and blades. The targets may be detectable by imaging, acoustically, electromagnetically, and/or by other suitable detection means. Furthermore, the targets may be active or passive. Examples of active targets include targets that emit light in an imaging system, targets that emit sound waves in an acoustic system, and targets that emit radio frequency energy in an electromagnetic system. Examples of passive targets include elements with reflective surfaces. With the guidance array 400 connected to the blades and the blades fixed securely to an underlying bone, the surgical navigation system can be used to track the underlying bone and the retractor system 10 within the surgical environment.

Figure 2:
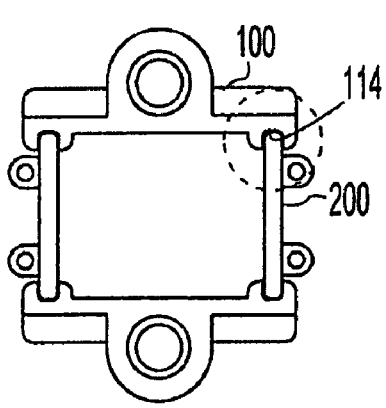
FIG. 2 is a top plan view of the retractor system of FIG. 1.

FIGS. 2-13 illustrate various configurations for assembling the blades 100, 200. FIG. 2 illustrates a top view of the assembled blades with the third and fourth blades 200 pressed into the grooves 114 of the first and second blades 100.

Figure 3:
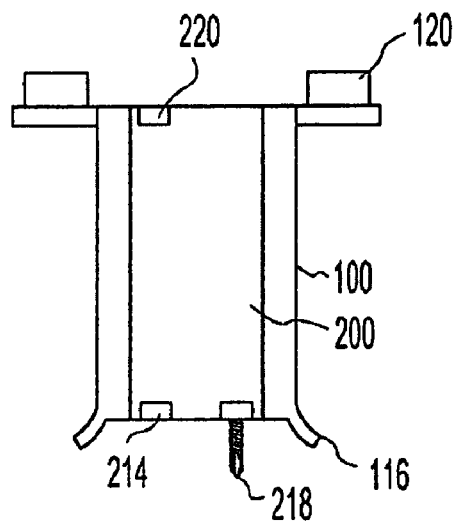
FIG. 3 is a side elevation view of the retractor system of FIG. 1.
Figure 4:
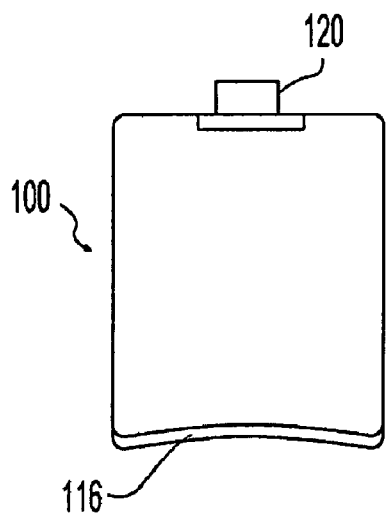
FIG. 4 is a front elevation view of the retractor system of FIG. 1.

FIGS. 3 and 4 illustrate side and front views of the blades showing the arrangement of the handle sockets 120, accessory tab 220, screw receiving tab 214, screw 218, and outturned tips 116.

Figure 5:
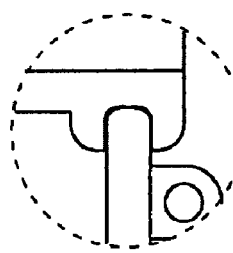
FIG. 5 is a detail view of the engagement of the blades of the retractor system of FIG. 1.

FIG. 5 is a detail view of the engagement of the third and fourth blades 200 with the grooves 114 showing a press fit.

Figure 6:
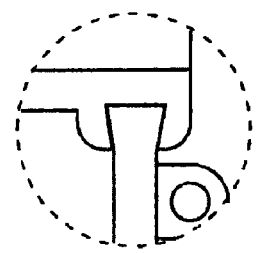
FIG. 6 is a detail view showing an alternative engagement of the blades of the retractor system of FIG. 1.

FIG. 6 is a detail view of the engagement of the third and fourth blades 200 with the grooves 114 showing an alternate arrangement defining a sliding dovetail.

Figure 7:
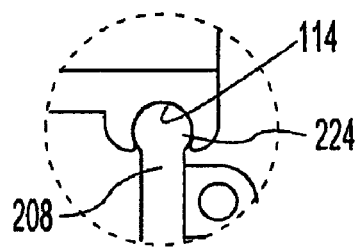
FIG. 7 is a detail view showing an alternative engagement of the blades of the retractor system of FIG. 1.

FIG. 7 is a detail view of the engagement of the third and fourth blades 200 with the grooves 114 showing an alternate cylindrical sliding arrangement. In the embodiment of FIG. 7, the lateral edges 208 of the third and fourth blades include an enlarged bull nose protrusion 224 defining greater than 180° of a cylinder and the grooves 114 define a cylindrical slot extending more than 180° for receiving the protrusion 224. The embodiment of FIG. 7 may be sized to allow pivoting of the blades relative to one another.

All of the embodiments shown in FIGS. 5-7 may be reversed so that the female engagement portion is on the third and fourth blades 200 and the male engagement portion is on the first and second blades 100.

Figure 8:
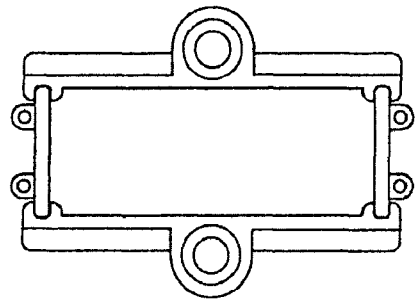
FIGS. 8-13 are top plan views showing alternate assembled configurations of the blades of the retractor system of FIG. 1.

FIG. 8 illustrates a blade assembly having greater width formed by substituting wider first and second blades for those of FIG. 1.

Figure 9:
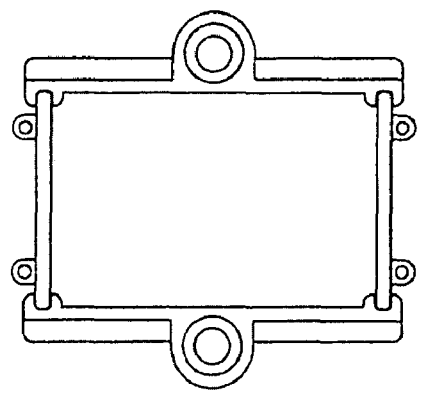

FIG. 9 illustrates a blade assembly having greater width and greater depth formed by substituting wider first, second, third, and fourth blades for those of FIG. 1.

Figure 10:
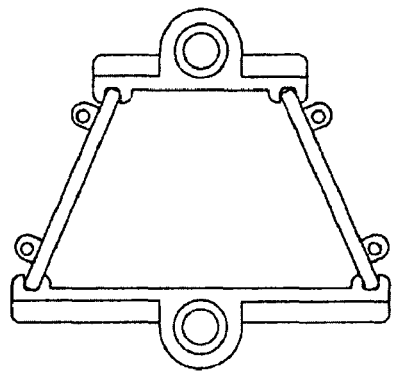

FIG. 10 illustrates a trapezoidal blade assembly formed by using first and second blades of differing widths.

Figure 11:
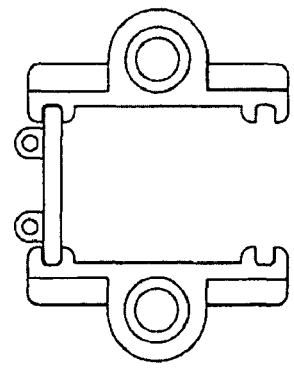

FIG. 11 illustrates an open blade assembly formed by using only a third blade to connect the first and second blades and leaving the opposite side open.

Figure 12:
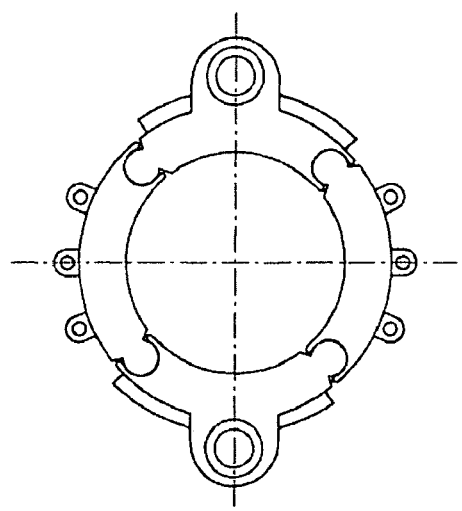

FIG. 12 illustrates a curved blade assembly formed by substituting curved blades for those of FIG. 1.

Figure 13:
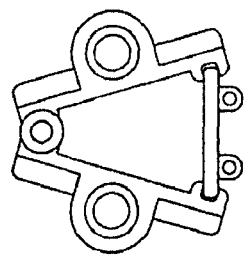

FIG. 13 illustrates a triangular blade assembly. In this embodiment, the first and second blades are pinned to one another such that as the blades are moved apart they pivot, or wedge, open. A third blade is engaged with the open side of the wedge to form a closed triangular retractor.

Figure 14:
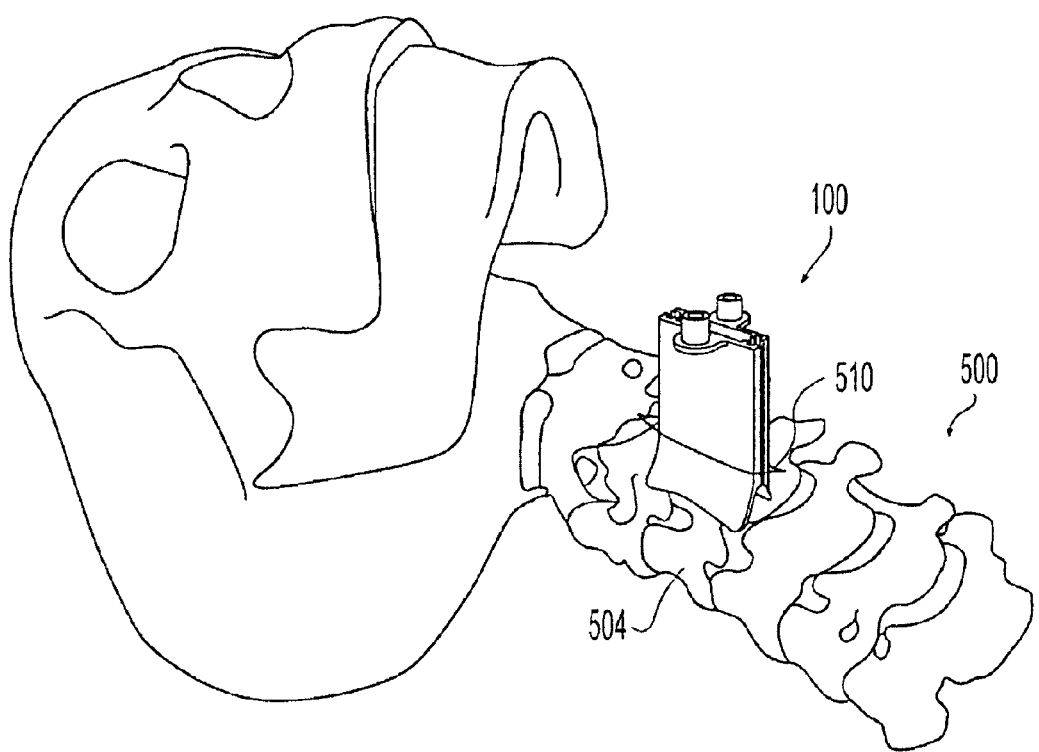
FIGS. 14-20 are perspective views showing the retractor system of FIG. 1 in use to gain access to a surgical site at an anterior portion of a cervical vertebra of a human spine.
Figure 15:
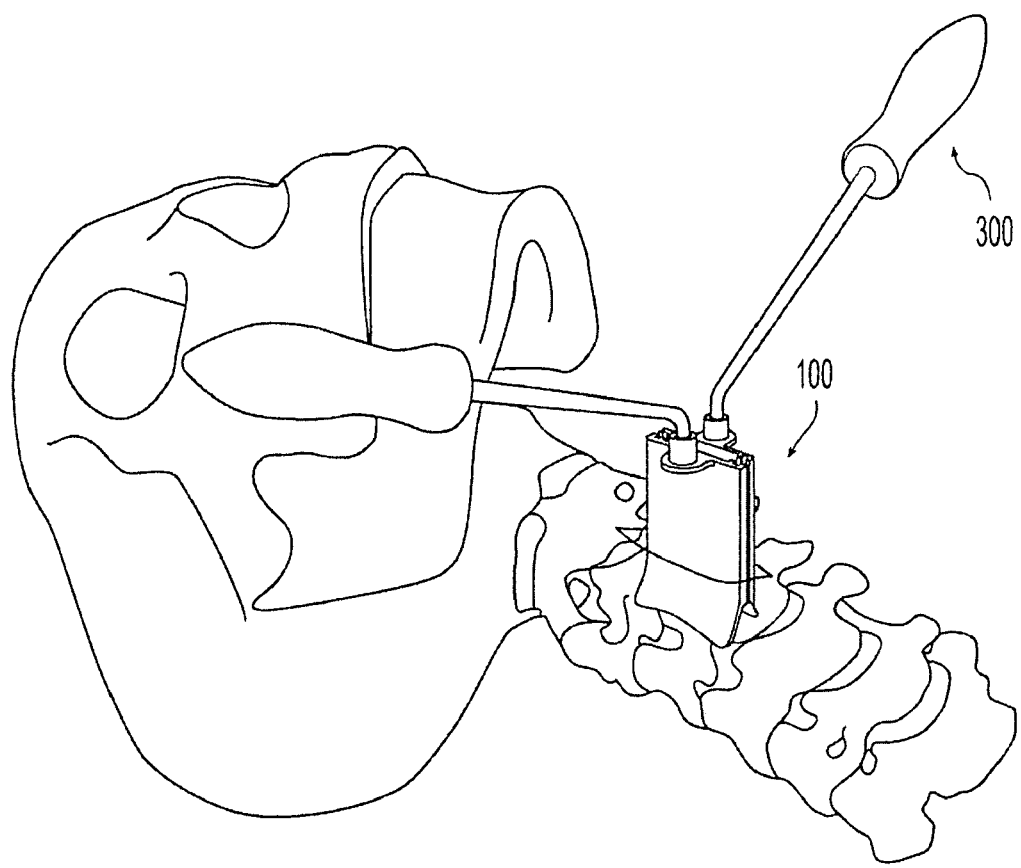
Figure 16:
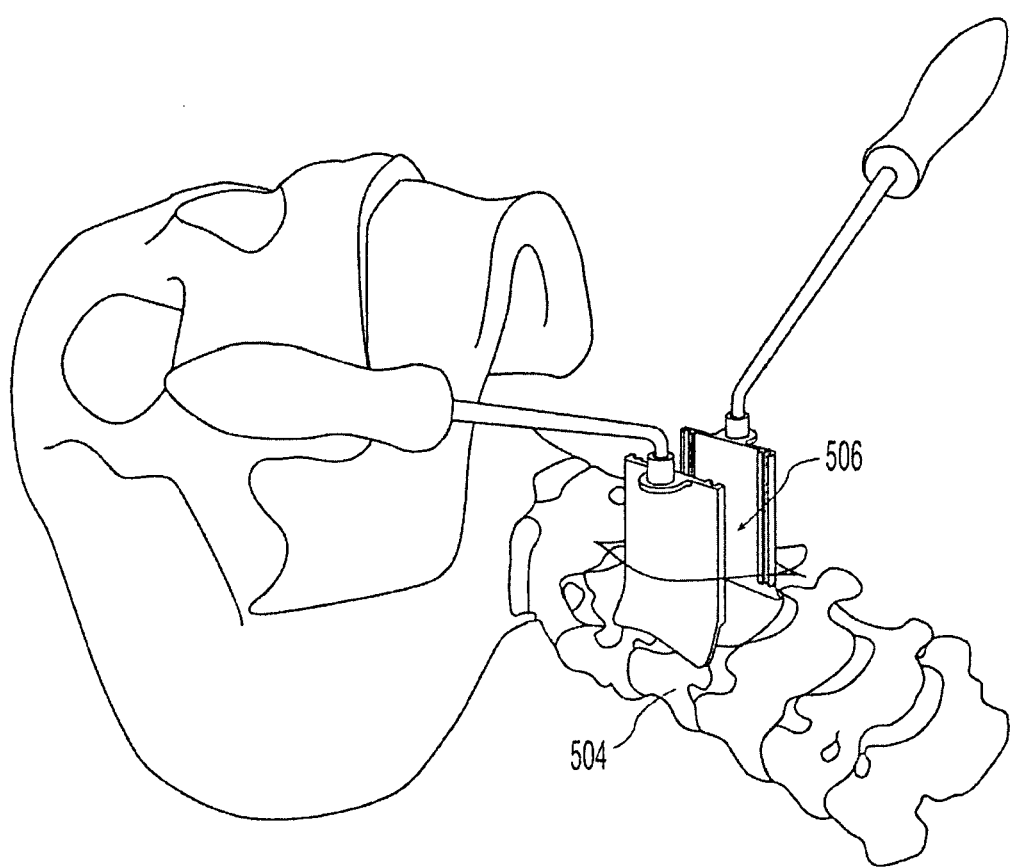
Figure 17:
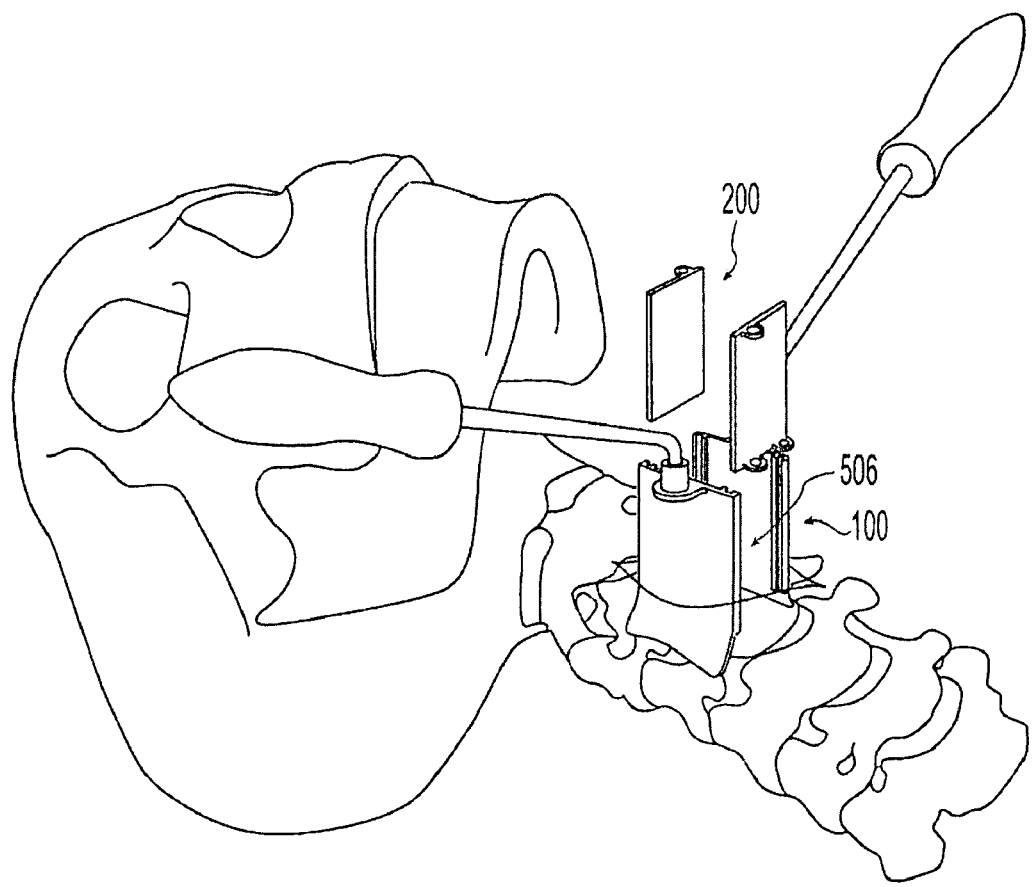
Figure 18:
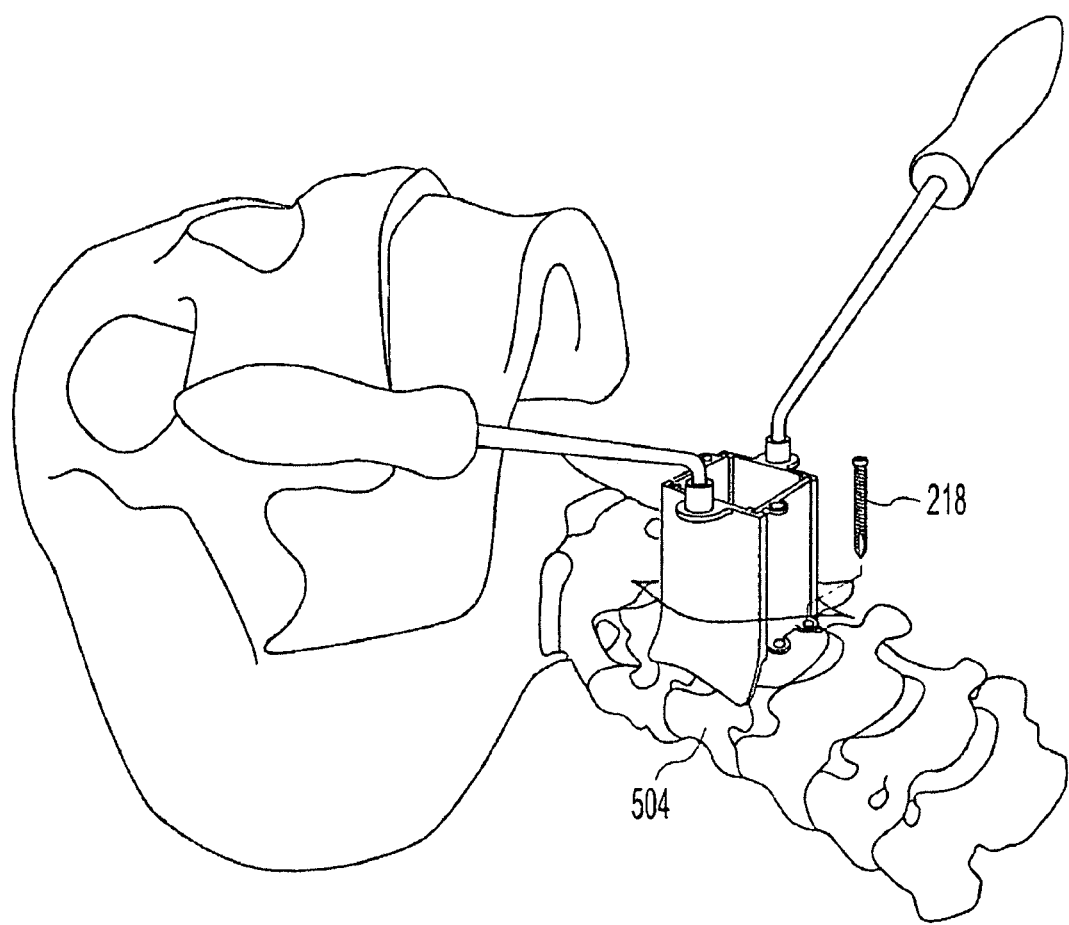
Figure 19:
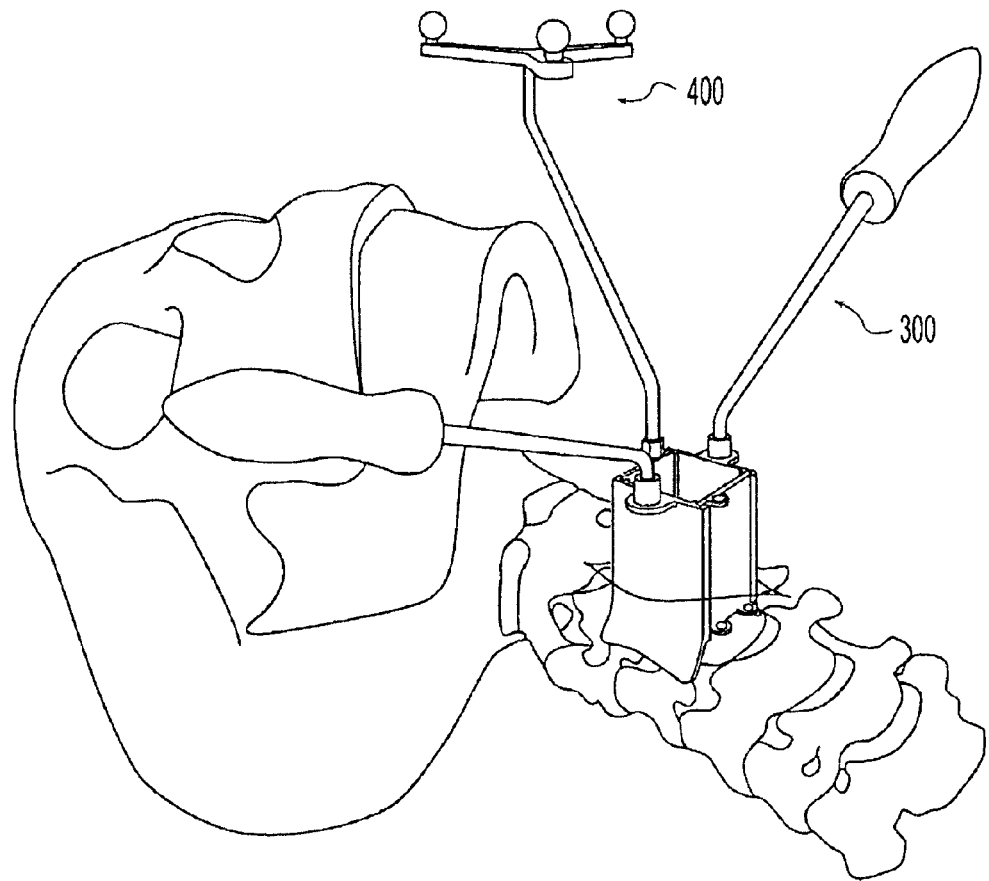
Figure 20:
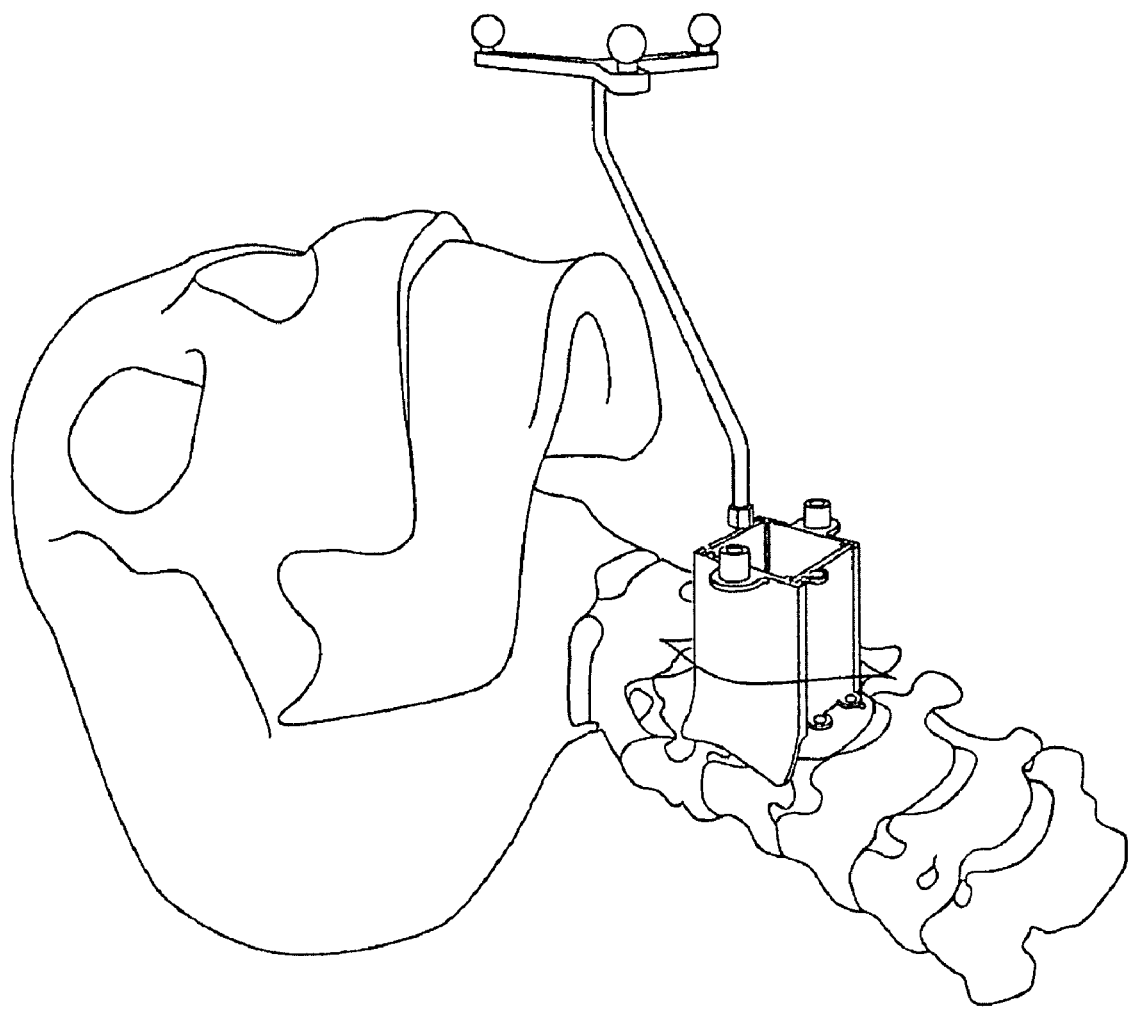

FIGS. 14-20 illustrate the retractor system of FIG. 1 in use to gain access to the anterior portion of the cervical spine 500. First and second blades 100 are placed together with their inwardly directed faces contacting one another. The blades 100 are then inserted through an incision 510 and through the underlying tissues until their distal ends 108 are adjacent a cervical vertebra 504 (FIG. 14). Handles 300 are then engaged with the first and second blades 100 (FIG. 15) and used to translate, pivot, and/or otherwise separate the first and second blades 100 to separate the tissues and develop a space 506 (FIG. 16) leading to the vertebra 504. One or more additional blades 200 are then engaged with the first blades 100 (FIGS. 17 and 18) to maintain the separation of the first blades 100 and/or further develop the space 506. One or more screws 218 may be placed to secure the blade assembly to the vertebra 504. The guidance array may be attached to the blade assembly (FIG. 19) to enable surgical navigation of the blade assembly and/or underlying vertebra. Finally, the handles 300 may be removed (FIG. 20) to provide easier access to the blade assembly and surgical site.

Although examples of a retractor system and its use have been described and illustrated in detail, it is to be understood that the same is intended by way of illustration and example only and is not to be taken by way of limitation. The invention has been illustrated in use to access a surgical site on the anterior side of a cervical vertebra. However, the retractor system may be configured for use at other locations within a patient's body. Accordingly, variations in and modifications to the retractor system and its use will be apparent to those of ordinary skill in the art, and the following claims are intended to cover all such modifications and equivalents.

What is claimed is:

1. A retractor system for holding open an incision at a surgical site, the retractor system comprising: a first retractor blade having a substantially flat rectangular body extending along a first insertion axis from a proximal end to a distal end, and a first longitudinal edge and a second longitudinal edge extending parallel to the first insertion axis between the proximal end and the distal end; a second retractor blade having a substantially flat rectangular body extending along a second insertion axis from a proximal end to a distal end, and a first longitudinal edge and a second longitudinal edge extending parallel to the second insertion axis between the proximal end and the distal end; wherein the first and second retractor blades include outturned distal tips; wherein the first retractor blade and the second retractor blade are separate components being independently positionable such that an inwardly directed face of the first retractor blade is capable of contacting an inwardly directed face of the second retractor blade to form a first position, and the first retractor blade and the second retractor blade are moveable between the first position in which they are nearer one another and a second position in which they are further from one another; and a third retractor blade having a substantially flat rectangular body extending along a third insertion axis from a proximal end to a distal end and extending normal to the third insertion axis between a first lateral edge and a second lateral edge, wherein the proximal end of the first, second and third retractor blades are spaced from the surgical site and the distal end of the first, second and third retractor blades are adjacent the surgical site; wherein the distal end of the third retractor blade being engageable with the proximal end of the first and second retractor blades in distal sliding relationship parallel to the insertion axis; wherein the first lateral edge of the third retractor blade is connectable to the first longitudinal edge of the first retractor blade and the second lateral edge of the third retractor blade is connectable to the second longitudinal edge of the second retractor blade when in the second position to maintain the first and second retractor blades in the second position, wherein the first, second, and third retractor blades defining an open space between them in which a surgical procedure may be carried out.

2. The retractor system of claim 1 further comprising a fourth retractor blade having a substantially flat rectangular body extending along a fourth insertion axis from a proximal end to a distal end and extending normal to the fourth insertion axis between a first lateral edge and a second lateral edge, wherein the first lateral edge of the fourth retractor blade is connectable to the second longitudinal edge of the first retractor blade, and the second lateral edge of the fourth retractor blade is connectable to the first longitudinal edge of the second retractor blade when in the second position, wherein the first, second, third, and fourth retractor blades defining a polygonal open space.

3. The retractor system of claim 1 wherein the third retractor blade frictionally engages the first and second retractor blades.

4. The retractor system of claim 1 wherein the third retractor blade engages the first and second retractor blades in sliding dovetail relationship.

5. The retractor system of claim 1 wherein the third retractor blade engages the first and second retractor blades in magnetic relationship.

6. A retractor system for defining a path to a surgical site on an anterior portion of a cervical spine, the retractor system comprising: a first retractor blade having a substantially flat rectangular body extending along a first insertion axis from a proximal end to a distal end, and a first longitudinal edge and a second longitudinal edge extending parallel to the first insertion axis between the proximal end and the distal end; a second retractor blade having a substantially flat rectangular body extending along a second insertion axis from a proximal end to a distal end, and a first longitudinal edge and a second longitudinal edge extending parallel to the second insertion axis between the proximal end and the distal end; wherein the first and second retractor blades include outturned distal tips; wherein the first retractor blade and the second retractor blade are separate components being independently positionable such that an inwardly directed face of the first retractor blade is capable of contacting an inwardly directed face of the second retractor blade to form a first position, and the first retractor blade and the second retractor blade are moveable between the first position in which they are nearer one another and a second position in which they are further from one another, the first and second retractor blades each including a handle removably mounted to the first and second blades; a third retractor blade having a substantially flat rectangular body extending along a third insertion axis from a proximal end to a distal end and extending normal to the third insertion axis between a first lateral edge and a second lateral edge, wherein the first lateral edge of the third retractor blade is connectable to the first longitudinal edge of the first retractor blade, and the second longitudinal edge of the third retractor blade is connectable to the second longitudinal edge of the second retractor blade when in the second position to maintain the first and second retractor blades in the second position; and a fourth retractor blade having a substantially flat rectangular body extending along a fourth insertion axis from a proximal end to a distal end and extending normal to the fourth insertion axis between a first lateral edge and a second lateral edge, wherein the first lateral edge of the fourth retractor blade is connectable to the second longitudinal edge of the first blade, and the second lateral edge of the fourth retractor blade is connectable to the first longitudinal edge of the second retractor blade when in the second position to maintain the first and second retractor blades in the second position, wherein the first, second, third, and fourth retractor blades defining an open space between them in which a surgical procedure may be carried out; wherein the proximal end of the first, second, third, and fourth retractor blades are spaced from the surgical site and the distal end of the first, second, third, and fourth retractor blades are adjacent the surgical site; wherein the distal end of the third retractor blade and fourth retractor blade being engageable with the proximal end of the first and second retractor blades in distal sliding relationship parallel to the insertion axis; at least one of the first, second, third, and fourth retractor blades including a fastener for engaging a cervical vertebra to secure the at least one blade to the cervical vertebra.

7. The retractor system of claim 1 wherein at least one of the first, second, and third retractor blades further comprises a fastener for attaching the at least one blade to tissue at the surgical site.

8. The retractor system of claim 7 wherein the fastener comprises a screw engageable with a bone to secure the at least one blade to an underlying bone.

9. The retractor system of claim 1 further comprising first and second handles removably attached to the first and second blades.

10. The retractor system of claim 1 further comprising a guidance array trackable by a surgical navigation system to indicate the location of the blade within the surgical environment.

11. The retractor system of claim 1 wherein at least one of the first, second, and third retractor blades further comprises a radiolucent material.

12. The retractor system of claim 1 wherein at least one of the first, second, and third retractor blades further comprises an insulating material.

13. The retractor system of claim 1 wherein the first and second retractor blades include grooves on opposed inner surfaces and the third retractor blade includes side edges that engage the grooves in the first and second retractor blades.

14. A retractor system for defining a path to a surgical site on an anterior portion of a cervical spine, the retractor system comprising:
    a first retractor blade having (i) a substantially flat rectangular body extending along a first insertion axis from a proximal end to a distal end, and (ii) a first longitudinal edge and a second longitudinal edge extending parallel to the first insertion axis between the proximal end and the distal end;
    a second retractor blade having (i) a substantially flat rectangular body extending along a second insertion axis from a proximal end to a distal end, and (ii) a first longitudinal edge and a second longitudinal edge extending parallel to the second insertion axis between the proximal end and the distal end;
    wherein the first and second retractor blades include outturned distal tips;
    wherein the first retractor blade and the second retractor blade are separate components being independently positionable such that a substantial portion of an inwardly directed face of the first retractor blade is capable of contacting a substantial portion of an inwardly directed face of the second retractor blade to form a first position to open the incision at the surgical site, and the first retractor blade and the second retractor blade are moveable between the first position in which they are nearer one another and a second position in which they are further from one another, the first and second retractor blades each including a handle removably mounted to the first and second blades;
    a third retractor blade having a substantially flat rectangular body extending along a third insertion axis from a proximal end to a distal end and extending normal to the third insertion axis between a first lateral edge and a second lateral edge, wherein the first lateral edge of the third retractor blade is connectable to the first longitudinal edge of the first retractor blade, and the second longitudinal edge of the third retractor blade is connectable to the second longitudinal edge of the second retractor blade when in the second position to maintain the first and second retractor blades in the second position; and
    a fourth retractor blade having a substantially flat rectangular body extending along a fourth insertion axis from a proximal end to a distal end and extending normal to the fourth insertion axis between a first lateral edge and a second lateral edge, wherein the first lateral edge of the fourth retractor blade is connectable to the second longitudinal edge of the first blade, and the second lateral edge of the fourth retractor blade is connectable to the first longitudinal edge of the second retractor blade when in the second position to maintain the first and second retractor blades in the second position, wherein the first, second, third, and fourth retractor blades defining an open space between them in which a surgical procedure may be carried out;
    at least one of the first, second, third, and fourth retractor blades including a fastener for engaging a cervical vertebra to secure the at least one blade to the cervical vertebra.

15. The retractor system of claim 14 further comprising a surgical navigation guidance array and wherein at least one of the first, second, third, and fourth retractor blades includes a mount engageable with the guidance array in fixed relationship.

* * * * *